US007291352B2

(12) United States Patent
Gow et al.

(10) Patent No.: US 7,291,352 B2
(45) Date of Patent: Nov. 6, 2007

(54) METHODS AND COMPOSITIONS FOR ORAL DELIVERY OF ARECA AND MATE' OR THEOBROMINE

(75) Inventors: Robert T. Gow, Naples, FL (US); John Pierce, Thousand Oaks, CA (US); George W. Sypert, Naples, FL (US)

(73) Assignee: HerbalScience LLC, Naples, FL (US)

( * ) Notice: Subject to any disclaimer, the term of this patent is extended or adjusted under 35 U.S.C. 154(b) by 240 days.

(21) Appl. No.: 10/945,378

(22) Filed: Sep. 20, 2004

(65) Prior Publication Data

US 2005/0089584 A1    Apr. 28, 2005

Related U.S. Application Data

(63) Continuation-in-part of application No. 10/818,439, filed on Apr. 5, 2004, which is a continuation-in-part of application No. 10/408,888, filed on Apr. 8, 2003, now abandoned, and a continuation-in-part of application No. 10/408,896, filed on Apr. 8, 2003, now abandoned, and a continuation-in-part of application No. 10/273,981, filed on Oct. 18, 2002, now Pat. No. 7,037,524, which is a continuation-in-part of application No. 10/263,579, filed on Oct. 3, 2002, now Pat. No. 7,029,707.

(60) Provisional application No. 60/514,187, filed on Oct. 24, 2003, provisional application No. 60/369,889, filed on Apr. 3, 2002, provisional application No. 60/326,928, filed on Oct. 3, 2001.

(51) Int. Cl.
A61K 36/00    (2006.01)
A61K 36/889   (2006.01)
A61K 31/44    (2006.01)

(52) U.S. Cl. ............. 424/774; 424/725; 424/727; 514/356

(58) Field of Classification Search ............ None
See application file for complete search history.

(56) References Cited

U.S. PATENT DOCUMENTS

| 4,064,253 A | 12/1977 | Khoe |
| 4,154,823 A | 5/1979 | Schutt |
| 4,248,861 A | 2/1981 | Schutt |
| 4,708,949 A | 11/1987 | Liu |
| 5,178,735 A | 1/1993 | Manabe et al. |
| 5,234,947 A | 8/1993 | Cherksey |
| 5,273,754 A | 12/1993 | Mann |
| 5,296,224 A | 3/1994 | Schwabe |
| 5,380,826 A | 1/1995 | Castor et al. |
| 5,389,371 A | 2/1995 | Shiao |
| 5,401,502 A | 3/1995 | Wunderlich et al. |
| 5,440,055 A | 8/1995 | Castor |
| 5,466,455 A | 11/1995 | Huffstutler, Jr. et al. |
| 5,512,285 A | 4/1996 | Wilde |
| 5,554,382 A | 9/1996 | Castor |
| 5,578,307 A | 11/1996 | Wunderlich et al. |
| 5,585,386 A | 12/1996 | Rosenbaum |
| 5,639,441 A | 6/1997 | Sievers et al. |
| 5,698,199 A | 12/1997 | Mori et al. |
| 5,720,974 A | 2/1998 | Makino et al. |
| 5,733,577 A | 3/1998 | Myers et al. |
| 5,750,709 A | 5/1998 | Castor |
| 5,770,207 A | 6/1998 | Bewicke |
| 5,776,486 A | 7/1998 | Castor et al. |
| 5,776,935 A | 7/1998 | Danysz et al. |
| 5,821,450 A | 10/1998 | Fedida |
| 5,854,064 A | 12/1998 | Castor et al. |
| 5,876,759 A | 3/1999 | Gowan, Jr. |
| 5,877,005 A | 3/1999 | Castor et al. |
| 5,891,465 A | 4/1999 | Keller et al. |
| 5,906,825 A | 5/1999 | Seabrook, Jr. et al. |
| 5,906,848 A | 5/1999 | Kreuter et al. |
| 5,976,550 A | 11/1999 | Engel et al. |
| 5,977,120 A | 11/1999 | Giles, Jr. |
| 6,008,249 A | 12/1999 | Gajdos et al. |
| 6,017,932 A | 1/2000 | Singh et al. |

(Continued)

FOREIGN PATENT DOCUMENTS

CN    1157103    *    8/1997

(Continued)

OTHER PUBLICATIONS

Ashraf-Khorassani, M. et al., "Supercritical Fluid Extraction of Kava Lactones from Kava Root and Their Separation Via Supercritical Fluid Chromatography", Chromatographia (1999), vol. 50, No. 5/6, pp. 287-292.

(Continued)

Primary Examiner—Christopher R. Tate
(74) Attorney, Agent, or Firm—Troutman Sanders LLP

(57) ABSTRACT

The present invention comprises methods and compositions comprising *Areca* extract compositions and compositions comprising extracts of *Ilex paraguariensis* or theobromine. Methods of the invention comprise methods of making pharmaceutical or nutriceutical products comprising *Areca catechu* extract compositions and maté extract compositions or theobromine, and methods of use of the extracted products and pharmaceutical and nutriceutical products. The present invention also comprises methods for treating conditions related to mental and physical fatigue and obesity, as well as, enhancement of mental focus, cognition, and a sense of well being, comprising administering the compositions of the present invention.

19 Claims, No Drawings

U.S. PATENT DOCUMENTS

| | | | |
|---|---|---|---|
| 6,024,998 A | 2/2000 | Kreuter et al. | |
| 6,025,363 A | 2/2000 | Giles, Jr. | |
| 6,045,825 A | 4/2000 | Cody | |
| 6,068,846 A | 5/2000 | Cho et al. | |
| 6,080,410 A | 6/2000 | Bewicke | |
| 6,095,134 A | 8/2000 | Sievers et al. | |
| 6,117,431 A | 9/2000 | Ramazanov et al. | |
| 6,126,940 A | 10/2000 | Takahashi et al. | |
| 6,140,375 A | 10/2000 | Nagahama et al. | |
| 6,143,300 A | 11/2000 | Stevonot | |
| 6,159,473 A | 12/2000 | Watkins et al. | |
| 6,174,542 B1 | 1/2001 | Hinton et al. | |
| 6,207,164 B1 | 3/2001 | Kreuter et al. | |
| 6,238,695 B1 | 5/2001 | Makooi-Morehead et al. | |
| 6,238,722 B1 | 5/2001 | Meadows | |
| 6,241,988 B1 | 6/2001 | Erdelmeier et al. | |
| 6,277,396 B1 | 8/2001 | Dente | |
| 6,280,736 B1 | 8/2001 | Erdelmeier et al. | |
| 6,288,109 B1 | 9/2001 | Chatterjee et al. | |
| 6,290,985 B2 | 9/2001 | Ream et al. | |
| 6,312,736 B1 | 11/2001 | Kelly et al. | |
| 6,352,713 B1 | 3/2002 | Kirschner et al. | |
| 2002/0192241 A1 | 12/2002 | Chen et al. | |
| 2002/0192316 A1* | 12/2002 | Altaffer et al. | 424/776 |
| 2003/0099756 A1 | 5/2003 | Gow et al. | |
| 2006/0195934 A1* | 8/2006 | Apuya et al. | 800/278 |
| 2006/0198800 A1* | 9/2006 | Dilallo et al. | 424/59 |

FOREIGN PATENT DOCUMENTS

| | | |
|---|---|---|
| CN | 1175354 | 3/1998 |
| EP | 987026 | 3/2000 |
| GB | 943121 | 11/1963 |
| JP | 63202367 | 8/1988 |
| JP | 63307892 | 12/1988 |
| JP | 05320063 | 12/1993 |
| JP | 08157384 | 6/1996 |
| JP | 09286734 | * 11/1997 |
| JP | 2002226403 | 8/2002 |
| KR | 2001058419 | 7/2001 |
| WO | WO 99/61038 | 12/1999 |
| WO | WO 00/72861 | 12/2000 |

OTHER PUBLICATIONS

Lopez-A Vila, Viorica et al., "Supercritical Fluid Extraction of Kava Lactones from *Piper Methysticum* (Kava) Herb", J. High Resol. Chromatogr. (1997), vol. 20, pp. 555-559.

Nguyen, Uy et al., "Extraction and Fraction of Spices Using Supercritical Fluid Carbon Dioxide", The 5$^{th}$ International Symposium on Supercritical Fluids, 1998, Nice, France.

Rosin, Miriam P., "The Influence of pH on the Convertogenic Activity of Plant Phenolics", Mutation Research (1984), vol. 135, No. 2, pp. 109-113.

Sardar, P.K. et al., "Thin Layer Chromatographic Detection of Gambier in *Acacia catechu*", Research and Industry (1984), vol. 29, No. 3, pp. 202-203.

Vanwyk, C.W. et al., "Observation on the Effect of Areca Nut Extracts on Oral Fibroblast Proliferation", Journal of Oral Pathology & Medicine (1994), vol. 23, pp. 145-148.

Grimmett, Christopher, "The Use of Liquid Carbon Dioxide for Extracting Natural Products", Chemistry and Industry Food Processing, vol. 10, pp. 359-362, (1981).

* cited by examiner

METHODS AND COMPOSITIONS FOR ORAL DELIVERY OF ARECA AND MATE' OR THEOBROMINE

RELATED PATENT APPLICATIONS

This application claims priority to U.S. Provisional Patent Application No. 60/514,187, filed Oct. 24, 2003, and is a continuation-in-part of U.S. patent application Ser. No. 10/818,439 filed Apr. 5, 2004, which is a continuation-in-part of U.S. patent application Ser. No. 10/408,888, filed Apr. 8, 2003 now abandoned, and is also a continuation-in-part of U.S. patent application Ser. No. 10/408,896, filed Apr. 8, 2003 now abandoned, and is a continuation-in-part of U.S. patent application Ser. No. 10/273,981, filed Oct. 18, 2002 now U.S. Pat. No. 7,037,524, which is a continuation-in-part of U.S. patent application Ser. No. 10/263,579, filed Oct. 3, 2002 now U.S. Pat. No. 7,029,707, which claims priority to U.S. Provisional Patent Application Nos. 60/326,928, filed Oct. 3, 2001, and 60/369,889, filed Apr. 3, 2002.

FIELD OF INVENTION

The invention relates to compositions derived from extracts of *Areca catechu* with characteristics different from those of native plant material. More specifically, the present invention relates to *Areca catechu* compositions combined with compositions comprising extracts of *Ilex paraguariensis* or maté, or theobromine, that exhibit benefits for memory, cognition, and a sense of well being, as well as therapy for obesity and as an appetite suppressant.

BACKGROUND OF INVENTION

*Areca*, a type of palm tree also known as *Areca catechu*, is generally cultivated in India, Southeast Asia, the East Indies, Taiwan and East Africa. The fruit of the *Areca* tree is a nut containing a single seed having a thin seed coat. The nut of *Areca catechu* tree contains several pyridine-derived alkaloids, including arecoline, arecaidine, guvacoline, and guvacine which may be as high as 1.7% of the nut's makeup. In nature, the highest single alkaloid component concentration in *Areca* nut is arecoline, which contains a methyl ester functional group.

The *Areca* nut is known around the world for its stimulating effects as well as improved cognition and memory, and it is chewed by almost one-half billion people who seek these properties of the nut. Betel quid is the combination of *Areca catechu* nut and Piper betel leaf, and other lesser components, and is the most common use of the *Areca* plant. Betel quid chewing, however, has been shown to be a major etiologic factor in oral cancer among such users. It has been found that *Areca* nut tannins and arecoline inhibit the growth of oral mucosal fibroblasts and keratinocytes. The effects of long-term use include oral submucosal fibrosis, leukoplasia and oral cancer. Studies have shown that conventional *Areca* nut extracts induce DNA breaks and unscheduled DNA synthesis and differentiation of oral keratinocytes. Arecoline also displays genotoxic effects.

The autonomic effects of *Areca* nut on the user when chewing betel quid, include sweating and facial flush, and increases in skin temperature and heart rate. Specifically, the alkaloids arecoline and arecaidine, although initially causing a brief depressor response, subsequently produce an increase in arterial blood pressure and heart rate. These stimuli are mediated through muscarinic M1 receptors. In animals, arecoline, Arecaidine, guvacoline, and guvacine are known to possess activity as agonists at muscarinic acetylcholine receptors. Additionally, arecoline has been shown to have indirect effects on catecholamine levels, while arecaidine and guvacine inhibit gamma-aminobutyric acid (GABA) receptor uptake in micromolar concentrations.

Other botanical constituents having stimulating effects are found in the holly family, Aquifoliaceae. The genus *Ilex* is one such member and is found worldwide in subtropical and tropical regions of both hemispheres. *I. paraguariensis*, a perennial tree, is native to South America and is also known as maté or yerba maté. It is the most commercialized plant of South America. *I. paraquariensis* is used to prepare a tea-like maté beverage. The maté beverage is made from the dried, toasted and milled leaves and stems of the plant genus and widely consumed in Argentina, Paraguay, Uruguay, Southern Brazil, and more recently in North America, Europe, and the Middle East.

The maté beverage is consumed primarily as an infusion, either by the addition of boiling water to the dry plant material, or by repeated additions of almost boiling water to the plant material. This infusion allows for extraction of water soluble plant constituents. Exposure of persons who drink the maté beverage to such extracted compounds is significant when the numbers of people and amount of maté beverage consumed is considered. A large number of people regularly consume some amount of maté beverage. In South America, approximately 30% of the population drink more than one liter per day of maté beverage, and many persons use the beverage as treatment of various conditions such a mental and physical fatigue, headaches, obesity, nervous depression, rheumatic pains, and improved cognition. The estimates for caffeine intake due to maté beverage consumption exceed the caffeine intakes known for other beverages such as coffee.

Consequently, one outcome of consumption of maté beverage and conventional nutraceutical extractions, is the presence of caffeine-related disorders such as gastrointestinal problems, caffeine toxicity, jitteriness, generalized anxiety, and insomnia. The consumption of caffeine exaggerates stress and stress-related hormone release. Blood pressure is elevated and the risks for heart attack and stroke are increased when caffeine is routinely consumed. Because maté beverage is such a part of the social structure and cultural habits of so many people and the fact that it is being increasingly used as a nutraceutical medicinal agent, reducing the amount of maté consumed does not appear to be a viable method for reducing caffeine consumption. An additional problem is that the maté that is consumed is made from raw maté plant material, which has varying amounts of caffeine when consumed drink to drink or dose to dose. This variability can cause confusing symptoms in users, hence, making the diagnosis of physiological problems difficult. In addition, such variability can cause uneven results when maté is used for treatment of various physiological conditions. A final issue regarding maté is that clinical and epidemiologic studies have found a positive association between maté consumption and cancer of the esophagus, oral cavity, pharynx, larynx, stomach and bladder.

Theobromine is best known for its effects in chocolate products. Theobromine has been synthesized and has been used as a drug to treat different medical conditions. For example, theobromine has been used as a diuretic making it particularly useful after a person has experienced cardiac failure. Cardiac failure often results in an excess accumulation of bodily fluids. Theobromine is also known for its ability to dilate blood vessels making it a commonly prescribed treatment for people suffering from high blood pressure. In addition, theobromine is known as a weak stimulant but does cause the jitteriness and hyper-anxiety associated with caffeine. As a stimulant, it has been noted to raise levels of serotonin making it an inexpensive anti-depressant. Theobromine also is an appetite suppressant and a useful adjunct for weight reduction. Theobromine remains in the body for a very long period of time. The half life after ingestion is approximately 6 hours. Another rather unique property of theobromine is its ability to relax bronchi in the lungs, which also has been used to treat asthmatic and pulmonary diseases. Theobromine has also been found to be relatively harmless in humans unless taken in excessive quantities.

What is needed then are compositions of combinations of extracts of *Areca* nut and extracts of maté, or extracts of *Areca* nut and theobromine, that provide desired physiological effects of improved memory, cognition and a sense of well being, appetite suppression, and have lowered amounts of carcinogens, such as arecoline and tannins. Such compositions would have medicinal value in improving mental focus and cognition, enhancing a sense of well being, reducing physical and mental fatigue and in treating obesity.

SUMMARY OF THE INVENTION

The present invention comprises methods and compositions of *Areca* extracts combined with maté extracts, or theobromine. Such compositions are provided for oral delivery in the form of tablets, capsules, lozenges, liquids, and emulsions to achieve a beneficial effect with a corresponding reduced incidence of dose related side effects.

An aspect of the present invention comprises methods of selective extraction of compounds such as tannins from extraction compositions of maté and *Areca* to yield compositions having a lower risk of cancer than the native plant materials. Another aspect of the present invention comprises compositions that are combinations of compositions of *Areca* extracts with maté extracts or combinations of *Areca* extract compositions and theobromine, or combinations of *Areca* extracts, maté extracts and theobromine.

An aspect of the present invention comprises methods and compositions comprising *Areca catechu* and maté. Methods of the invention comprise methods of extraction of compounds from plant source material of *Areca catechu* and maté, methods of making pharmaceutical or nutriceutical products comprising *Areca catechu* and maté, and methods of use of the extracted products, and pharmaceutical and nutriceutical products made from extract compositions. Compositions of the present invention comprise extraction products of *Areca catechu* comprising extracted alkaloid compounds that have altered alkaloid profiles that are not found in natural plant material, combined with compositions comprising compounds isolated from the plant material of maté or compositions comprising theobromine. An embodiment of the compositions of the present invention comprises compositions comprising an extract of *Areca catechu* which is higher in the soluble carboxylic acid alkaloids than in the less soluble ester compounds of *Areca*, in combination with compositions of maté that have reduced amounts of caffeine when compared to native maté plant materials, or the *Areca* extract in combination with theobromine, or a combination of all three, *Areca*, maté and theobromine. Compositions of the present invention also comprise pharmaceutical and nutriceutical compositions such as a rapid-dissolving tablet containing a combination of extracts of *Areca catechu* and extracts of mate, or combinations of extracts of *Areca catechu*' and theobromine.

An aspect of the present invention also comprises methods of selective extraction of compounds such as tannins from extracts of *Areca* or maté to yield compositions that have a lowered risk of cancer than the natural plant materials. Another aspect of the present invention comprises compositions comprising extraction products of *Areca* combined with extraction products of maté having alkaloid compositions that are not found in native plant material, and that have reduced carcinogenicity.

Another aspect of the present invention comprises methods for making compositions comprising *Areca* compositions combined with maté compositions that have a predetermined characteristic, such as a lowered amount of caffeine compared to maté plant materials or a lower amount of tannins compared to the *Areca* and maté plant materials. Compositions of the present invention comprise caffeine amounts that are lower than or equal to the amount of theobromine present in the unextracted maté plant material, and also comprise compositions comprising a predetermined amount of caffeine wherein the amount of caffeine is lower than or equal to the theobromine amount.

The compositions of the present invention comprise *Areca* compositions combined with maté compositions that have a predetermined characteristic, such as an alkaloid amount, that is unlike that found in the unextracted native plant material and in currently known extracted compositions, such as beverage infusions and decaffeinated products. Compositions having differing predetermined alkaloid amounts allow for the production of *Areca* compositions combined with maté compositions having differing alkaloid amounts for enhancing or reducing certain physiological effects when the compositions are administered. Embodiments of the compositions provide compositions comprising *Areca* compositions combined with maté compositions having a caffeine amount that is lower than or equal to the amount of theobromine, and compositions comprising *Areca* compositions combined with maté compositions having a lowered amount of tannins compared to the *Areca* and maté plant materials. Accordingly, an aspect of the present invention relates to methods of selective extraction of the tannin compounds of *Areca* and maté thereby reducing the risk of oral, esophageal, gastric and bladder cancers associated with excessive *Areca* or maté consumption.

Another aspect of the present invention relates to formulation of oral delivery systems having the desired clinical effects of enhancing memory, cognition, and sense of well being as well as treatments for obesity and mental or physical fatigue. The compositions of the present invention can be used to make a combined *Areca* extract and maté extract or theobromine composition product in formulations such as a paste, resin, oil or powder, beverage, liquid infusion or decoction, or a dry flowable powder. Such products are processed for many different uses, and some embodiments are made into a fast-dissolve tablet or other orally available delivery vehicle. The *Areca* or maté plant material is extracted and the resulting *Areca* or maté compositions from the extractions of each, have a predetermined alkaloid amounts and can be in the form of a paste, oil or resin, or other form suitable for use or further processing. Preferably, the extraction methods include using supercritical $CO_2$ extraction and solvent modifiers such as water and ethyl alcohol. The extracted compositions, having predetermined alkaloid amounts, can then be subjected to further processing steps. Maté and *Areca* compositions produced by such methods have predetermined characteristics, such as alkaloid ratios or profiles, that are unlike those found in the native plant materials and the alkaloid profile can be tailored to meet particular considerations for the final product. The *Areca* and maté compositions so produced can be used alone or in combination with other compounds or other extracted materials, herbal remedies, pharmaceutical agents, food, dietary supplements, or beverages. The *Areca* and maté compositions can also be used in treatments of physiological conditions.

DETAILED DESCRIPTION

The present invention comprises methods and compositions of *Areca catechu*, particularly the *Areca* nut, and maté or theobromine. As used herein, "*Areca*" or "*Areca catechu*" refers to the nut or seed of the *Areca catechu* palm tree. Methods of the present invention comprise making compositions comprising extracted *Areca* compositions, which include both the materials extracted from *Areca* and the extracted residue, combined with extracted maté compositions, or *Areca* extract compositions and theobromine. Compositions of the present invention comprise compositions resulting from extraction of *Areca*, such as compositions of extracted *Areca* that have ratios of alkaloid compounds that are not found in the native plant material, in combination with maté extract compositions. Suitable methods and compositions of *Areca catechu* and maté are disclosed in U.S. patent application Ser. Nos. 10/818,439, 10/408,888, 10/408,896, and PCT/US04/010733 and PCT/US02/33385, U.S. Provisional Patent Application No. 60/514,187, and U.S. and international applications which claim the priority of U.S. Provisional Patent Application No. 60/514,187, and the disclosures of each are hereby incorporated by reference in its entirety as if specifically set forth herein.

The present invention comprises extracting the nut of *Areca catechu*, using extraction steps that include transformation of the arecoline (an alkaloid methyl ester) into arecaidine (an alkaloid carboxylic acid) and guvacoline (an alkaloid methyl ester) into guvacine (an alkaloid carboxylic acid), compositions comprising an *Areca* extract having decreased percentages of arecoline and guvacoline, and compositions in which lipids and tannins present in native *Areca* plant material are removed, producing end products that are different from the native plant materials. Such end products exhibit the desired pharmacological activities without the risk of oral cancer associated with *Areca* ingestion.

The present invention comprises compositions comprising extracts of the nut of the *Areca catechu* palm combined with compositions comprising extracts of maté, or extracts of *Areca* in combination with theobromine. Another aspect of the present invention comprises methods of use of compositions comprising combinations of *Areca* compositions and maté or theobromine compositions for the enhancement of memory, cognition, and a sense of well being, as well as for the treatment of fatigue and appetite suppression. More specifically, the present invention comprises methods and compositions of combinations of *Areca* compositions having alkaloid profiles not found in the native plant material and compositions of maté comprising altered alkaloid profiles. The present invention also comprises methods and compositions of combinations of *Areca* compositions having alkaloid profiles not found in the native plant and maté compositions, such combination compositions may be substantially devoid of arecoline, guvacoline, tannins or caffeine. Native plant materials include plant materials that may be shredded, ground or powdered after picking and drying, but no extractions, other than incidental water or oil loss, due to the physical manipulation of the plant material, are included, the term "alkaloid profile" shall mean the ratios of alkaloid compounds found in either *Areca* or maté, and the relative amounts of each compound in relation to the other alkaloid compounds in that plant material. The alkaloid profile refers to the amount in grams of each alkaloid compound found in *Areca* or maté. The native plant material, which has not undergone extractions to remove any components, would have an alkaloid profile exhibiting the types and amounts of alkaloid compounds made by the plant. An altered alkaloid profile or an alkaloid profile different from that of native plant material means the ratios of the alkaloid compounds of the composition are different from the ratios found in the native plant material. For example, in an altered alkaloid profile, the amount of one or more alkaloid compounds may be different or the ratios of one or more alkaloid compounds to the total amount or to other alkaloid compounds are different from that found in native plant material.

Compositions of the present invention comprise compositions of *Areca catechu*, combined with compositions maté extracts, or *Areca* compositions in combination with theobromine, in formulations such as a paste, powder, or in other forms, for use in dietary supplements. The compositions can be processed to produce consumable items, for example, by mixing it in a food product or in a capsule, or providing the paste itself for use as a dietary supplement, with sweeteners and flavors added as appropriate. Accordingly, such supplements may include, but are not limited to, compositions of *Areca* combined with maté or theobromine compositions for oral delivery in the form of tablets, capsules, lozenges, liquids, and emulsions. A dry, flowable powder formulation is also contemplated by the present invention. Other aspects of compositions of the present invention comprise *Areca catechu* compositions combined with maté extract compositions, or theobromine, in the form of a rapid-dissolve tablet.

The present invention comprises compositions comprising extracts of Areca. Methods of making such extracts are taught in patents applications cited herein and by other methods known to those skilled in the art. Compositions of *Areca* may comprise the alkaloids of the *Areca* nut. Methods of extracting *Areca* may include steps comprising supercritical fluids extraction. Other extraction steps may include the transformation of the arecoline (an alkaloid methyl ester) into arecaidine (an alkaloid carboxylic acid), and the transformation of guvacoline (an alkaloid methyl ester) to guvacine (an alkaloid carboxylic acid).

The extracted *Areca* compound compositions have characteristics that are different than the native plant material. For example, an aspect of the compositions of the present invention includes compositions comprising an *Areca catechu* extract having an altered alkaloid ratio. For example, compositions comprising an *Areca catechu* extract having a decreased percentage of arecoline and a decreased percentage of guvacoline, when compared to native plant material, are contemplated. Other compositions comprise alkaloid ratios between the methyl ester alkaloids and the carboxylic acids that are different from native plant materials.

The *Areca* nut, like many nuts, contains a high level of lipids. These lipids are a complicating factor in the extraction of water-soluble compounds from *Areca* nuts. The *Areca* nut comprises approximately 0.2% to 1.7% by weight alkaloid compounds. Of that amount, approximately 40-85% is arecoline, 10 to 40% is arecaidine and guvacine is 2 to 30%. Other alkaloids present include guvacoline and areaolidine. For example, a measurement of the nut reveals that the total alkaloid content is approximately 1.14% mass of the dried nut, then of that alkaloid content, approximately 26.5% is guvacine, 25.6% is Arecaidine, and 47.9% is arecoline. Other compounds present in the nut include tannins, which are water soluble compounds that comprise about 20%, by weight, of the nut.

One method of extracting the desired alkaloid compounds from the nut comprises a solvent extraction step comprising extracting a dried powder of *Areca* nut with water at about 10° C. to 80° C., for approximately 15 minutes to approximately 150 minutes, and preferably at least 60 minutes. A pH adjustment step may occur during or after the solvent extracting step to convert the ester alkaloid compounds into carboxylic acid alkaloid compounds. This extraction step yields an extraction product composition comprising alkaloids, tannins and a low amount of lipids. Tannins are removed from this composition by the addition of adsorbents, such as fining with albumin, activated charcoal, or by anion exchange resins. After removal of the tannins, a pH adjustment step may occur. A pH adjustment step, used for converting ester compounds into carboxylic acid compounds comprises adjusting the pH to at least a pH of 12, optionally in the presence of a reducing agent, such as ascorbic acid, and at a temperature of 50° C., for a time period of not less than 15 minutes. It is this step that converts the ester compounds into the carboxylic acid compounds, such as arecoline to arecaidine. The amount of conversion can be determined by measuring the initial content of the ester compounds, such as arecoline, and then adding the amount of base necessary to convert the desired percentage of the ester compounds, arecoline, to the carboxylic compound, arecaidine. After the conversion, the pH is then lowered to approximately pH 6-8. The conversion of ester compounds to carboxylic compounds is also used to convert guvacoline to guvacine.

Another process for extracting arecoline, arecaidine, guvacoline and guvacine from the *Areca catechu* comprises supercritical extraction. The *Areca catechu* nut is isolated from the plant, dried, and then ground into a powder. The powder is then dissolved in alcohol and subjected to supercritical $CO_2$ extraction procedure. The pressure and temperature are stabilized from between about 200 bar to about 600 bar and about 20° C. to about 70° C. The resulting extracted *Areca* material may be in a paste, oil, or resin form and is collected. The spent supercritical extractant can either be recycled for future use or vented into the atmosphere. The extractant-to-feed ratio (kg of extractant versus kg of *Areca catechu*) may range from about 5:1 to about 100:1.

The *areca* extract composition of the present invention may be produced by several methods. In one method, the *areca* nut is ground and then undergoes alcohol solvent extraction, and the solvent, containing extracted *areca* compounds, is freeze-dried. The solid material is discarded, or can be used for other extractions. The freeze-dried material then undergoes SFE (Supercritical Fluids Extraction) to substantially remove the lipid compounds, leaving the alkaloids and other water-soluble compounds in the residue. The residue is then dissolved in water to solubilize the tannins, alkaloids and other water-soluble compounds, and the tannins are removed by protein precipitation, resins or other known methods. The aqueous solution, which contains substantially no tannin compounds, is then freeze-dried or concentrated by known methods, and is referred to herein as the *Areca* extract composition.

The *Areca* extract material is then suspended in water and mixed vigorously for a period between about 10 minutes to about 60 minutes to produce and maintain micron-sized particles. The temperature of the water may be from room temperature to about 70° C. to facilitate efficient mixing and ester cleavage. A suitable chemical base is added to raise the pH of the aqueous solution to a pH of between about 8.0 to about 12.0. The pH of the solution is then held for a period of time between about 15 minutes to about 2.5 hours. The pH of the aqueous solution is then returned to a neutral pH using a suitable acid.

Compositions of the present invention comprise compositions resulting from the extraction of *Areca catechu* nut. The *Areca* and maté compositions include both the extract product resulting from extractions methods and the residue from the extraction, including plant material that was extracted and intermediary extracted residues from subsequent extractions. *Areca* extract compositions comprise extracted products that have an altered alkaloid profile that is different from the native plant material. An aspect of *Areca* extract compositions of the present invention comprises compositions that have an alkaloid profile of more carboxylic acid alkaloids than ester alkaloids. For example, compositions of the present invention comprise extracts of *Areca* nut that have a higher percentage of arecaidine than arecoline, and compositions that comprise a higher percentage of guvacine than guvacoline. Compositions of the present invention also comprise alkaloids, tannins and a small amount of lipids. Such compositions may or may not comprise alkaloids wherein the carboxy alkaloids are found in a higher percentage than ester alkaloid compounds. Compositions of the present invention also comprise the residue of extracted *Areca* nut from which at least one compound has been removed, such as tannins, alkaloids or some lipids. Accordingly, an aspect of the present invention comprises compositions comprising the residue of the extracted *Areca* nut that is substantially devoid of tannins, guvacoline, or arecoline, or comprise residues wherein tannins, guvacoline and arecoline are substantially reduced from the amounts found in unextracted *Areca* plant material, or comprise residues wherein tannins, guvacoline and arecoline are less than 10% of the amounts found in unextracted *Areca* plant material.

Compositions of the present invention comprise *Areca* extract compositions wherein the arecoline content is from approximately 0% to approximately 99% of the arecaidine content. Compositions also comprise *Areca* extract compositions wherein the ester alkaloid content is from approximately 0 to approximately 99% of the carboxy acid alkaloid content. Compositions of the present invention also comprise *Areca* extract compositions wherein the guvacoline content is from approximately 0 to approximately 99% of guvacine content.

Compositions of the present invention comprise *Areca* extract compositions comprising alkaloid compounds. Such alkaloids include, but are not limited to, arecoline, arecaidine, areaolidine, guvacine, and guvacoline. Compositions also comprise other compounds, including but not limited to caffeine, theobromine, and theophylline, and herbs or extractions of herbs or other plant materials such as extracts of kava, chocolate, sage, sage oil, guarana, muira puama, and maca.

The value of the alkaloid make-up for a sample of an *Areca catechu* extract can be determined using conventional analytical techniques, such as high performance liquid chromatography and/or gas chromatography or any other technique known to one of ordinary skill in the art.

Compositions of the present invention comprise extracted *Areca catechu* nut compositions that are different from the native *Areca catechu* nut, the native plant material. As used herein, native plant material is *Areca* plant material or maté plant material that has not been extracted by solvents or other processes that would alter the chemical nature of the plant material, other than picking the plant material and drying it. For example, the present invention comprises a composition, comprising an extract of *Areca* wherein the alkaloid profile is different from that of native *Areca* plant material. The present invention further comprises *Areca* extract compositions wherein the amount of carboxy acid alkaloid compounds is greater than the amount of ester alkaloid compounds, compositions wherein the amount of ester alkaloid compounds is less than that of native *Areca* plant material, compositions wherein the amount of arecoline is less than the amount of arecaidine, compositions wherein the amount of guvacoline is less than the amount of guvacine, and compositions wherein the amount of arecoline and guvacoline is less than the amount of arecaidine and guvacine.

The present invention also comprises methods and compositions of maté or theobromine combined with one or more of the *Areca* extract compositions described herein. As used herein, maté refers to the plant or plant material derived from the plant Aquifoliaceae, *Ilex* genus, wherein the genus includes but is not limited to, *I. paraguariensis, I. theezans* C. Martis ex Reisseck, *I dumosa* Reisseck; *I dumosa* Reisseck var *dumosa; I. argentina* Lillo; *I. brevicuspis* Reisseck; *I. microdonta* Reisseck; *I. paraguariensis* St. Hil. var. *paraguaraniensis; I. paraguariensis* St. Hil. var. *vestita* (Reiss.); and *I. pseudobuxus* Reisseck. The term also includes all clones, cultivars, variants, and sports of *Ilex*. The term "*Ilex*" is also used interchangeably with "maté" and means these plants, clones, variants, sports, etc. As used herein, when the tea-like beverage made from this plant genus is referred to, the beverage is designated as "maté beverage". Compositions of the present invention preferably comprise extracts of the leaf of *I. paraguariensis*.

The compositions of the present invention are useful in providing the physiological effects of enhanced memory, improved cognition, reduced mental and physical fatigue, a sense of well being, and appetite suppression. Though each plant material, *Areca* and maté, has been consumed by humans for some of these effects, the present invention provides compositions that are essentially free from carcinogens such as the tannin compounds and arecoline, or at least have greatly reduced amounts of such compounds, and also provide effects different from the natural plant materials, for example, due to the lack of caffeine.

Compositions of the present invention comprise alkaloid extracts of the *Areca catechu* nut and maté. Alkaloids include, but are not limited to, arecoline, arecaidine, guvacoline, guvacine, caffeine, theophylline, and theobromine. An aspect of the present invention comprises compositions having lowered amounts of arecoline in relation to the levels found in native *Areca* plant materials. Another aspect of the present invention comprises compositions of *Areca* extract compositions with substantially reduced tannins and maté extract compositions with substantially reduced tannins. As used herein, "substantially reduced" means at least 50% of the compound or compounds have been removed. Preferably at least 70% of the compounds such as tannins have been removed in such compositions, and most preferred are compositions wherein at least 90% of the compounds have been removed. Yet another aspect of the present invention comprises compositions of maté extracts having a lowered caffeine concentration and substantially reduced tannins in relation to the concentrations found in the native maté plant material. Compositions also comprise *areca* extract compositions combined with theobromine.

Compositions of the present invention comprise maté extracts of the leaf of *I. paraguariensis*. An aspect of the present invention comprises compositions of maté extracts of the leaf of *I. paraguariensis* having a lowered concentration or amount of caffeine in relation to the concentration or amount found in the native plant material. Another aspect of the present invention comprises compositions of maté extracts of the leaf of *I. paraguariensis* having reduced or substantially no tannin compounds in relation to the concentration or amounts found in the native plant material.

The present invention comprises compositions of maté extracts, and compositions of theobromine. Theobromine may be derived from maté, other sources, or be made by synthetic means known to those skilled in the art. Purine alkaloids, also referred to herein as methylxanthines, such as caffeine (1,3,7-trimethyl-xanthine), theobromine (3,7-dimethyl-xanthine) and theophylline (1,3-dimethyl-xanthine) are synthesized in many higher plants.

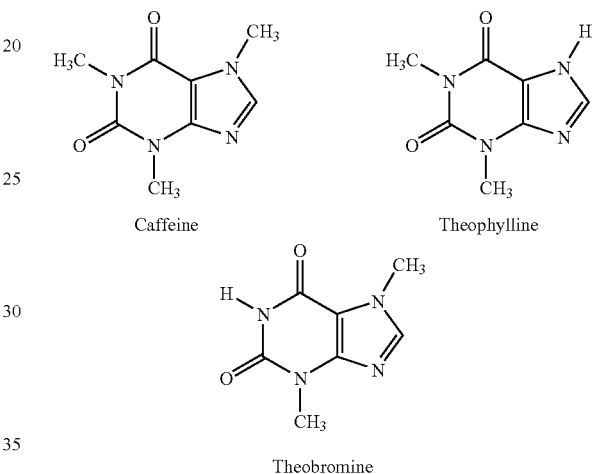

Caffeine          Theophylline

Theobromine

These three alkaloids, along with other methylxanthines, vitamins, minerals, fats, carbohydrates, proteins, nucleic acids and other plant cell constituents, are found in maté plant material. In the maté plant, the amounts of each alkaloid and the ratios of one to the others is variable and is dependent upon such factors as genetic variability, environmental conditions, harvest period, and other factors that influence the growth of plants. Additionally, the industrial processing methods used to make commercial products from maté plants cause further changes in the chemical constituency of the products. As used herein, the term "maté constituents" shall mean chemical compounds found in maté and shall include all such chemical compounds identified above as well as all other compounds found in maté. The native maté plant material has variable and unknown amounts of such alkaloid compounds, and the processing of the plant material introduces more variability in the amounts of alkaloid compounds found in the products that are consumed. This increased variability in the products consumed leads to widely fluctuating physiological changes in humans and animals ingesting such products, hinders effective treatments using maté products or prevents avoidance of unwanted physiological effects from ingestion of maté products.

Principal bioactive chemical constituents of maté are listed in Table 1. Though not wishing to be bound by any particular theory, it is currently believed that beneficial effects of aqueous maté extracts include protecting low density lipoprotein (LDL) from oxidative damage and can inhibit the atherosclerotic process. The maté effect (18.5 mM) has been found to be greater than that measured for red wine (0.74 mM). Maté extracts have been shown in in vitro assays to inhibit peroxidation in a concentration dependent manner which should protect cell membrane lipids as well as having a red blood cell protectant effect against hydrogen peroxide generated free radicals. It is thought that the antioxidant activity is due to caffeoyl derivatives. Maté may also play a protective role in the process of glycation. Glycation has been proposed as a key to diabetic complications resulting from hyperglycemia. The chlorogenic acids of maté have been demonstrated to be potent and selective inhibitors of HIV integrase and the polyphenols have been shown to inhibit formation and growth of neoplasms. Maté has also been demonstrated to possess conentation dependent vasorelaxing activity, diuretic effects, bronchial smooth muscle relaxation and reduction in appetite with increase in liver metabolic processes.

TABLE 1

Principal Bioactive Chemicals of *I. paraguariensis*

| Constituents | % Dried Weight |
| --- | --- |
| Methylxanthines | |
| Caffeine | 0.5-2.2 |
| Theobromine | 0.03-0.6 |
| Theophylline | 0.004-0.08 |
| Caffeoyl Derivatives | 9.0-11.0 |
| Saponin Glycosides | 5.0-10.0 |
| Tannins | 7.0-14.0 |

Compositions of the present invention comprise extracts of *Areca catechu*, combined with extracts of maté, or theobromine, as a paste, powder, or in other forms, which allows the compounds in the extract, such as alkaloids, to be used in dietary supplements. The extracts can be processed to produce such consumable items, for example, by mixing it in a food product or in a capsule, or providing the paste itself for use as a dietary supplement, with sweeteners and flavors added as appropriate. Accordingly, such supplements may include, but are not limited to, compositions of *Areca* extracts combined with maté extract compositions, or theobromine for oral delivery in the form of tablets, capsules, lozenges, liquids, and emulsions. Other aspects of compositions of the present invention comprise *Areca catechu* extracts combined with maté extract compositions or theobromine in the form of a rapid-dissolve tablet.

Compositions of the present invention comprise combinations of the extract compositions of *Areca* with extract compositions of maté or *Areca* extract compositions combined with theobromine. Compositions of the present invention comprise one or more compounds of *Areca* extracts in combination with one or more compounds of maté extract compositions. The compositions of *Areca* extracts or the maté extract compositions may have one or more of the altered alkaloid profiles taught herein. As used herein, the term "one or more compounds" means that at least one compound, such as arecaidine or theobromine is intended, or that more than one compound, for example arecaidine and guvacine, or theobromine and theophylline is intended. As is known in the art, the term "compound" does not mean one molecule, but multiples or moles of molecules of one or more compounds.

The present invention comprises compositions comprising combinations of maté compositions and *Areca catechu* compositions, wherein at least one of the compositions, for example either the maté composition or the *Areca* composition, has a different compound profile, or different compound amounts, than the native plant material. Further, compositions of the present invention may comprise at least one maté or *Areca* compositions that has the same compound profile or same compound amounts as are found in the native plant material. For example, a composition of the present invention may comprise an *Areca* extract composition with the altered profile or altered amounts of one or more compound of any of those taught or suggested herein in combination with a maté composition that has the profile or compound amounts of native maté plant material. The maté compositions range from compositions of maté plant material that has not undergone any extraction of compounds, other than drying the plant material, to maté extract compositions that have undergone one or more extraction steps taught herein. Also for example, a composition of the present invention may comprise a maté extract composition with the altered profile or altered amounts of one or more compounds of any of those taught or suggested herein in combination with an *Areca* composition that has the profile or compound amounts of native *Areca catechu* plant material that has been picked and dried. The *Areca* compositions range from compositions of *Areca* plant material that has not undergone any extraction of compounds, other than drying the plant material, to *Areca* extract compositions that have undergone one or more extraction steps taught herein. The compositions of the present invention also comprise the combination of one or more of the *Areca* compositions with one or more of the maté compositions with theobromine. Such combinations include all three types of compositions, *Areca*, maté and theobromine, or combinations of any two types of compositions, *Areca* with maté, *Areca* with theobromine, maté with theobromine.

The present invention comprises compositions comprising a combination of one or more compounds found in maté with extracts of *Areca catechu*, comprising arecoline, arecaidine, guvacoline and guvacine in concentrations that are different from those concentrations found in native *Areca* plant material, or with extracts wherein the amounts of arecoline and guvacoline are less than the amounts of arecaidine and guvacine. The present invention comprises *Areca* extract compositions, comprising an alkaloid profile comprising an arecoline component, an arecaidine component, a guvacoline component, and a guvacine component, wherein the alkaloid profile has a ratio of the arecaidine component to the arecoline component by weight of greater than about 1.0. The present invention also comprises ingestible products that comprise the compositions comprising areca extracts and maté extract compositions taught herein. For example, the present invention comprises compositions comprising a rapid dissolve tablet, comprising an *Areca* extract composition having an alkaloid profile wherein the carboxy acid alkaloid compounds are in a higher concentration than the ester alkaloid compounds and a maté extract composition wherein the caffeine has been removed or reduced to amounts lower than the amounts of theobromine, and wherein the amount of tannin compounds is reduced or substantially no tannins are present.

In another embodiment of the present invention, compositions comprise maté extract compositions in combination with *Areca* extract compositions. The areca extract compositions may comprise different ratios of arecoline, arecaidine, guvacoline and guvacine. *Areca* extract compositions having 0% arecoline and 100% arecaidine can be combined with the maté extract compositions. Similarly, *Areca* extract compositions having ratios of 99:1 arecaidine to arecoline or guavacine to guavacoline, and ratios including 98:2, 97:3, 96:4, 80:20, 70:30; 60:40; greater than 50% arecaidine or guavacine, to arecoline or guavacoline, and all the ranges therein between, and so on, may be used.

The present invention comprises compositions and methods for making and using such combination *areca* extract and maté extract compositions, where the compositions comprise oral delivery dosage formulations comprising the compositions taught herein. An aspect of the present invention comprises a rapid dissolve tablet, comprising a composition of maté extract composition in combination with an *Areca* extract composition, or theobromine combined with an *Areca* extract composition, wherein the *Areca* extract composition has an alkaloid profile wherein the carboxy acid alkaloid compounds are in a higher concentration than the ester alkaloid compounds.

Each and every one of the *Areca* compositions disclosed herein can be combined with compositions of maté extracts or with theobromine alone. Accordingly, an aspect of the present invention comprises extractions of maté for combining with the *Areca* extraction compositions described herein. Steam distillation techniques that are known to those skilled in the art may be used obtain extracts of maté from the maté plant material. The maté plant material may be the aerial portion of the plant, which includes the leaves, stems, flowers, branches, twig and trunk, or other plant parts, though leaves and stems are preferred starting material. The extract can be obtained from the maté leaves via the process of steam distillation of the leaves or by liquid extraction techniques such as using dichloromethane or petroleum ether as the extracting solvent. Alternatively, an extract of the dried leaf material can be prepared using carbon dioxide in the liquid or supercritical phase, or, a liquefied gas such as tetrafluoroethane or propane. In the case of carbon dioxide, the pressure ranges from about 1500 psi to over about 5000 psi, and in the case of the other liquefied gasses the pressure is an order of magnitude less ranging from about 50 psi to about 400 psi. The extract-laden liquid is then passed through a collection vessel wherein the liquefied gas can be collected as a vapor leaving behind the desired extract that was contained in the leaf. Although the maté extract may be obtained from any species of from the *Ilex* genus, the extract is preferably obtained from *I. paraguariensis*.

Alternatively, the chemical constituents found within maté, such as, but not limited to, caffeine or theobromine, can be purchased individually from a chemical supply company. For example, purified theobromine that has been extracted from a natural source, such as Cacoa, may be obtained commercially from the company Natra. Chemically synthesized theobromine can also be obtained from many different chemical supply companies such as Sigma Aldrich. The individual chemical constituents found in maté may be purchased and combined with the *Areca* extract compositions described herein. Such chemical constituents may also be mixed in the proportions that exist in maté prior to combining with the *Areca* extract compositions described herein.

The present invention comprises methods for producing compositions of maté extracts that have predetermined characteristics, including but not limited to, predetermined concentrations or amounts of alkaloid compounds. Embodiments comprise compositions of maté having a caffeine concentration that is less than or equal to the theobromine concentration in the maté composition. The amounts of methylxanthines present in maté are generally known. The amounts of methylxanthines found in the leaves of *Ilex paraguariensis*, on a dry weight basis, range from approximately 0.002% to 0.015% theophylline; 0.30% to 0.60% theobromine; and 0.80% to 2.00% caffeine. Compositions of the present invention comprise extracted maté compositions having predetermined caffeine concentrations, that when compared on an equal weight basis to the native plant material of equal to or approximately less than 0.60%, approximately less than 0.55%; approximately less than 0.50%; approximately less than 0.45%; approximately less than 0.40%; approximately less than 0.35%; approximately less than 0.30%; approximately less than 0.25%; approximately less than 0.20%; approximately less than 0.15%; approximately less than 0.10%; in the maté extract composition the amount of caffeine can include all ranges from 0% to less than or equal to the concentration or amount of theobromine in the maté extract composition.

Methods for producing such compositions comprise extraction of maté plant material to alter the amount of one or more compounds from an amount or amounts found in the native plant material, preferably such compounds comprise alkaloid compounds, and most preferably, such compounds comprise caffeine. These compositions include both the extract product resulting from extractions methods and the residue from the extraction, including plant material that was extracted and. intermediary extracted residues from subsequent extractions.

The native maté plant material may undergo pre-extraction steps to render the material into a form more easily extracted, though that form is not limited to any particular form, and any form that is useful for extraction is contemplated by the present invention. Such pre-extraction steps include, but are not limited to, wherein the material is chopped, minced, shredded, ground, pulverized, cut, or torn, and the starting material, prior to pre-extraction steps, is dried or fresh plant material. Another pre-extraction step includes soaking the plant material so that the plant material has a prescribed desired water content. A preferred pre-extraction extraction step comprises cutting the maté leaves into small pieces known as tea cut. The starting material or the pre-extraction material can then be dried or can have moisture added to it. Once the plant material is in a form for extraction, methods of extraction are contemplated by the present invention and are taught in U.S. Provisional Patent Application 60/514,187, and in applications claiming priority to U.S. Provisional Patent Application 60/514,187.

An aspect of the present invention comprises methods for extracting the maté plant material to remove one or more of the methylxanthines as well as flavor compounds and optionally, other compounds found in maté. This resulting extraction composition, denoted herein as "an extracted maté composition" preferably comprising a composition comprising a methylxanthine concentration wherein the concentration of caffeine is less than or equal to the concentration of theobromine, does not comprise the extracted plant material, but only the components, or compounds, extracted from the plant material. The extracted maté composition, comprising extracted methylxanthines, and/or flavor compounds and other compounds, is formulated with known pharmaceutical agents to provide a pharmaceutical composition. The pharmaceutical composition has an effective amount of one or more of the extracted methylxanthines, preferably having a caffeine concentration that is equal to or less than the theobromine concentration. An aspect of the invention comprises maté compositions having a lower amount of caffeine in relation to the level found in conventional leaf extracts. Methods of decaffeination have been well documented in the case of coffee. Descriptions of such methods are described in Katz. S N., "Decaffeination of Coffee", *Coffee: Technology*, Ed. Clark R J and Macrae R., New York, Elsevier Applied Science, 1987; and Pintauro N D., *Coffee Solubilization: Commericial Process and Techniques*, Park Ridge, Noyes Data Corporation, 1975; the teachings of which are incorporated herein by reference as if entirely set forth. As with coffee, the process of decaffeination of the leaves of maté can be accomplished in a similar fashion.

Another embodiment of the invention comprises maté compositions having reduced or substantially no tannins in relation to the level found in the native plant material or in maté beverages. To remove the tannins from the maté plant material, or from the decaffeinated extract of maté, fining with albumin, or adsorbents such as activated charcoal, or anion exchange resins are added. For a person skilled in the art, the removal of tannins through the addition of such adsorbents is accomplished in a straightforward manner by using hot water in a manner described as a decoction or infusion. The methods described herein above for removing tannins from *Areca* may be used for removing tannins from the extract of maté. In order to prepare a finished product for consumption, it is often beneficial to remove the water from the extract that has been prepared. The water may be removed using techniques known to those skilled in the art such as, but not limited to, vacuum distillation, spray drying, refractive window drying, or freeze drying of the product having reduced caffeine levels and substantially no tannins in relation to the levels found in the leaf material.

Other compositions of the present invention comprise extracted maté plant materials. Embodiments of extracted plant materials comprise maté that has undergone extraction methods described herein to remove compounds so that the extracted plant material has a predetermined characteristic, such as a predetermined alkaloid profile, particularly a methylxanthine concentration, in the remaining plant materials. An embodiment comprises extracted maté plant material that comprises a methylxanthine profile wherein the caffeine concentration is less than or equal to the theobromine concentration. As used herein, a maté extract composition is intended to include the composition comprising extracted maté plant materials or the composition comprising the extraction composition resulting from extraction of maté plant material. Either maté composition can be used in the present invention and the compositions are interchangeable unless otherwise indicated.

In general, the maté plant material that was extracted with supercritical $CO_2$, having an altered caffeine concentration, is recovered and further extracted with a hydroalcoholic solution in any one of the methods described below. An aspect of the compositions made using these methods is a composition comprising an altered alkaloid profile, and preferably an alkaloid profile wherein the amount of caffeine is less than or equal to the amount of theobromine in the composition.

In one method, extracted maté leaf material is mixed into a hydroalcoholic solution, which is 50% to 95% ethyl alcohol content in water, and preferably between 75% and 90% ethyl alcohol content, in a ratio of solution to maté material (liters:kg) ranging from 2:1 to 20:1. The mixture of leaf material and hydroalcoholic liquid is heated from 20° Celsius (C.) to 60° C., and mixed for a period of time of between 1 hour and 12 hours. One method for mixing comprises using a kettle that is jacketed such that the temperature is controlled. The kettle is closed and the mixture is stirred slowly. After the desired time of mixing, the liquid is separated from the solid material by means known to those skilled in the art, including but not limited to, filtration or centrifugation. The remaining solid material may be further extracted one or more times by the above steps of hydroalcoholic solution, heating and mixing to yield extracted maté compositions that can be used independently or can be pooled with other extracted maté compositions. Alternatively, the resulting material from the hydroalcoholic extraction methods can undergo supercritical $CO_2$ extraction, refrigerant extraction or other extractions to yield extracted maté compositions that can be used independently or pooled with other extracted maté compositions. An aspect of the compositions made using this method is a composition comprising an altered alkaloid profile, and preferably an alkaloid profile wherein the amount of caffeine is less than or equal to the amount of theobromine in the composition.

A further embodiment of a hydroalcoholic extraction method of the present invention comprises separate solutions of water and alcohol in a Soxhlet or pseudo-Soxhlet extraction process. The Soxhlet extraction process is a well known method for extracting materials. The Soxhlet extraction process or pseudo-Soxhlet extraction process can occur under normal atmospheric or reduced atmospheric pressure. In the Soxhlet extraction process the leaf material is held apart from the reservoir of solvent and a condenser element is above the leaf material onto which the solvent condenses and drips onto, into, and through the leaf material making the extract that collects into the reservoir below. This extraction process can be performed sequentially with water first and alcohol thereafter and then pooling the two individual liquid extracts, or alcohol first, followed by water, and then pooling the extracts. The resulting extracted maté composition from the Soxhlet extraction methods can undergo further extractions, including but not limited to, supercritical $CO_2$ extraction, refrigerant extraction or other extractions, to yield extracted maté compositions. The remaining solid material may also be further extracted one or more times by the Soxhlet extraction methods, or other extractions methods, to yield extracted maté compositions that can be used independently or pooled with other extracted maté compositions. An aspect of the compositions made using this method is a composition comprising an altered alkaloid profile, and preferably an alkaloid profile wherein the amount of caffeine is less than or equal to the amount of theobromine in the composition.

In performing the extraction methods above, it was found that the dried bulk hydroalcoholic extract of the leaves of *Ilex paraguariensis* amounts to between 10% to 30% by weight (excluding the carrier material) of the original dried *Ilex paraguariensis* leaves used. Using extraction methods such as those disclosed above, the desired alkaloid profiles are created in the maté extract compositions, whether it is the extracted maté compositions or in the extracted plant material compositions. Alternatively, the maté plant material could be extracted to remove one, two or all or almost all of at least three methylxanthines, caffeine, theophylline and theobromine, to produce either an extracted maté composition substantially free of one or more of these compounds, to produce an extracted plant material composition free of one or more of these compounds, or to produce a composition comprised of at least one, two or three of methylxanthines. The specific extraction environments, rates of extraction, and solvent used depends on the starting profile of the source material and the degree of profile change desired. Specific solvent and environmental attributes can be determined by those of ordinary skill in the art using no more than routine experimentation typical for adjusting a process to account for, e.g., variations in the attributes of starting materials that is to be processed to produce an output material that has specified attributes. For example, in a particular lot of maté plant material, the initial concentrations of caffeine, theobromine and theophylline are determined using methods known to those skilled in the art, such as by extraction and measurement of each using chromatography such as high performance liquid chromatography. One skilled in the art can determine the amount of change from the initial concentrations of methylxanthines to the predetermined amounts of methylxanthines for the final product and the extraction methods, as disclosed herein, to reach the desired profile of the final maté compositions. See Table 2.

TABLE 2

| Mate' Constituents (% dry weight) | | | | |
|---|---|---|---|---|
| | Caffeine | Theobromine | Theophylline | Tannins |
| Mate' Feedstock | 2.0 | 0.5 | 0.1 | 12.0 |
| Extract Post-Supercritical $CO_2$ | 0.8 | 1.1 | 0.2 | 8.0 |
| Extract Post-Fining (albumin) | 1.0 | 1.3 | 0.3 | 1.0 |

An embodiment of a composition comprises a maté extract composition having a predetermined caffeine concentration that is less than or equal to the original theobromine concentration that is found in the native plant material, or a predetermined theobromine concentration such as that which can result from extraction techniques taught herein, and comprises substantially no tannin compounds.

The maté extract composition, having a predetermined alkaloid profile and substantially reduced tannin compounds, can be processed to produce consumable items, for example, by mixing it in a food product or in a capsule, or providing the extracted maté plant material itself or an extracted maté composition for use as a dietary supplement, or beverage with sweeteners and flavors added as appropriate. According to a further aspect of the invention, the maté extract composition can be further processed to produce a dry, flowable powder. The powder can be used as a dietary supplement that can be added to various edible products. The powder or the final predetermined unique extract of maté is also suited for use in a rapid dissolve tablet.

According to a particular aspect of the invention, the maté extract composition is produced to have a predetermined alkaloid profile, preferably having a caffeine concentration less than or equal to the concentration of theobromine, that is particularly well suited for delivery in the oral cavity of human subjects, e.g., via a rapid dissolve tablet. Additionally, the maté extract composition may or may not have substantially reduced amounts of tannin compounds present.

Once a dry powder, comprising areca extract compositions, maté extract compositions, theobromine compositions, or combinations of two or more of these compositions, is obtained, it can be used in a variety of ways such as a dietary supplement, for tableting for addition to food substances or for other uses. In a particular embodiment, the powder is mixed with other ingredients to form a tableting composition of powder which can then be formed into tablets. In a particular embodiment, the tableting powder is first wet with a solvent comprising alcohol, alcohol and water, or other suitable solvents, in an amount sufficient to form a thick doughy consistency. Suitable alcohols include, but are not limited to, ethyl alcohol, isopropyl alcohol, denatured ethyl alcohol containing isopropyl alcohol, acetone, and denatured ethyl alcohol containing acetone.

The resulting paste is then pressed into a tablet mold. An automated molding system, such as described in U.S. Pat. No. 5,407,339 can be used. The tablets are then removed from the mold and dried, preferably by air-drying for at least several hours at a temperature high enough to drive off the solvent used to wet the tableting powder mixture, typically between about 70° C. to about 85° C. The tablets can then be packaged for distribution.

The *Areca* extract compositions and maté extract compositions or theobromine can be combined using techniques and methods that are known in the art. Such techniques include, but are not limited to, mixing, blending, stirring, including mechanical stirring, and dissolving.

Methods and compositions of the present invention comprise compositions comprising combinations of compositions of *Areca* and maté or theobromine in the form of a paste, resin, oil, or powder. An aspect of the present invention comprises compositions of liquid preparations of *Areca* extract compositions combined with liquid preparations of maté extract compositions or theobromine. Liquid preparations for oral administration may take the form of, for example, solutions, syrups or suspensions, or they may be presented as a dry product for reconstitution with water or other suitable vehicles prior to administration. Such liquid preparations may be prepared by conventional means with pharmaceutically acceptable additives such as suspending agents (e.g. sorbitol syrup, methyl cellulose, or hydrogenated edible fats); emulsifying agents (e.g. lecithin or acacia); non-aqueous vehicles (e.g. almond oil, oily esters or ethyl alcohol); preservatives (e.g. methyl or propyl p-hydroxybenzoates or sorbic acid); and artificial or natural colors and/or sweeteners. Compositions of the liquid preparations can be administered to humans or animals in pharmaceutical carriers known to those skilled in the art. Such pharmaceutical carriers include, but are not limited to, capsules, lozenges, syrups, sprays, rinses, and mouthwash.

An aspect of the present invention comprises compositions of a dry powder extract of *Areca* combined with a dry powder extract of maté or a dry powder comprising theobromine. Such dry powder compositions may be prepared according to methods disclosed herein and by other methods known to those skilled in the art, such as, but not limited to, spray air drying, freeze drying, vacuum drying, and refractive window drying. The combined dry powder compositions can be incorporated into a pharmaceutical carrier such as, but not limited to, tablets or capsules, or reconstituted in a beverage such as a tea.

Although the extraction techniques described herein are discussed in terms of *Areca* and maté, it should be recognized that compositions of the present invention can also comprise, in the form of a dry flowable powder or other forms, extracts from other plants such as, but not limited to, varieties of ginseng, cherry, lettuce, Echinacia, piper betel leaf, muira puama, ginger, willow, suma, damiana, horny goat weed, ginkgo biloba, turmeric, garlic, puncture vine, arctic root astragalus, eucommia, gastrodia, and uncaria, or pharmaceutical or nutriceutical agents.

The present invention comprises compositions comprising combinations of *Areca* extract compositions and maté extract compositions or theobromine compositions in tablet formulations, and methods for making such tablets. A tableting powder can be formed by combining between about 18% to about 60% by weight of the powdered *Areca* extract composition and about 1% to about 40% by weight of the powdered maté extract composition, or a theobromine composition, with between about 30% to about 80% by weight of a dry water-dispersible adsorbant such as, but not limited to, magnesium carbonate, or a dilutent, such as, but not limited to, lactose. Other dry tablet additives, such as, but not limited to, one or more of a sweetener, flavoring and/or coloring agents, a binder, such as acacia or gum arabic, a lubricant, a disintegrant, and a buffer, can also be added to the tableting powder. The dry ingredients are screened to a particle size of between about 50 to about 150 mesh. Preferably, the dry ingredients are screened to a particle size of between about 80 to 100 mesh.

A wide variety of tablet formations can be made. Preferably, the tablet has a formulation that results in a rapid dissolution or disintegration in the oral cavity. The tablet is preferably of a homogeneous composition that dissolves or disintegrates rapidly in the oral cavity to release the extract content over a period of about 2 seconds or less to about 60 seconds or more, preferably about 3 to about 45 seconds, and most preferably between about 5 to about 15 seconds.

Various rapid-dissolve tablet formulations known in the art can be used. Representative formulations are disclosed in U.S. Pat. Nos. 5,464,632; 6,106,861; 6,221,392; 5,298,261; 6,221,392; and 6,200,604; the entire contents of each are expressly incorporated by reference herein as if specifically set forth. For example, U.S. Pat. No. 5,298,261 teaches a freeze-drying process. This process involves the use of freezing and then drying under a vacuum to remove water by sublimation. Preferred ingredients include hydroxyethylcellulose, such as Natrosol from Hercules Chemical Company, added to between 0.1% and 1.5%. Additional components include maltodextrin (Maltrin, M-500) at between 1% and 5%. These amounts are solubilized in water and used as a starting mixture to which is added a composition comprising a combination of an *Areca* extract composition and a maté extract composition or theobromine composition, or individually the *areca* extract composition and the maté extract composition or theobromine composition, along with flavors, sweeteners, such as Sucralose or Acesulfame K, and emulsifiers such as BeFlora and BeFloraPlus which are extracts of mung bean.

A particularly preferred tableting composition or powder contains about 10% to about 60% by weight of a *Areca* extract powder and a maté extract powder, or a theobromine composition, and about 30% to about 60% of a water-soluble diluent. Suitable diluents include lactose, dextrose, sucrose, mannitol, and other similar compositions. Lactose is a preferred diluent but mannitol adds a pleasant, cooling sensation and additional sweetness in the mouth. More than one diluent can be used. A sweetener can also be included, preferably in an amount of between about 3% to about 40% by weight depending on the desired sweetness. Preferred sweetening substances include, but are not limited to, sugar, saccharin, sodium cyclamate, aspartame, and Stevia extract, used singly or in combination, although other sweeteners could alternatively be used. Flavorings, such as mint, cinnamon, citrus (e.g., lemon or orange), can also be included, preferably in an amount between about 0.001% to about 1% by weight. If a coloring is desired, natural and/or synthetic colors can be added, preferably in an amount of between about 0.5% to about 2% by weight.

Typically, this tableting composition will maintain its form without the use of a binder. If needed, however, various binders are suitable and can be added in an amount of between about 5% to about 15% by weight, or as necessary. Any binder known to one of ordinary skill in the art may be used. Preferred binders include, but are not limited to, acacia or gum arabic. Alternative binders include sodium alginate, extract of Irish moss, panwar gum, ghatti gum, mucilage of isapol husks, carboxymethylcellulose, hydroxyethylcellulose, methylcellulose, polyvinylpyrrolidone, VEEGUM.® (available from R. T Vanderbilt Co., Inc. of Norwalk, Conn.), larch arabogalactan, gelatin, Kappa carrageenan, copolymers of maleic anhydride with ethylene or vinyl methyl ether.

A tablet according to this aspect of this invention typically does not require a lubricant to improve the flow of the powder for tablet manufacturing. However, if it is so desired a lubricant may be provided. Any lubricant known to one of ordinary skill in the art may be used. Preferred lubricants include, but are not limited to, talc, magnesium stearate, calcium stearate, stearic acid, hydrogenated vegetable oils, and carbowax in amounts of between about 2% to about 10% by weight.

Similarly, a disintegrant is not expected to be necessary to produce rapid dissolve tablets using the present tablet composition. However, a disintegrant can be included to increase the speed with which a resulting tablet dissolves in the mouth. Any disintegrant known to one of ordinary skill in the art may be used. If desired, between about 0.5% to about 1% by weight of a disintegrant can be added. Preferred disintegrants include, but are not limited to, starches, clays, celluloses, algins, gums, crosslinked polymers (including croscarmelose, crospovidone and sodium starch glycolate), VEEGUM.® HV, agar, bentonite, natural sponge, cation exchange resins, aliginic acid, guar gum, citrus pulp, and sodium lauryl sulphate.

It is also generally considered unnecessary to buffer the tablet composition. However, a buffer may be beneficial in specific formulations. Any buffering agent known to one of ordinary skill in the art may be used. Preferred buffering agents include, but are not limited to, mono- and di-sodium phosphates and borates, basic magnesium carbonate and combinations of magnesium and aluminum hydroxide.

In a preferred implementation, the tableting powder is made by mixing in a dry powdered form the various components as described above, e.g., active ingredient (extract), diluent, sweetening additive, and flavoring, etc. An overage in the range of about 10% to about 15% of the active extract of the active ingredient can be added to compensate for losses during subsequent tablet processing. The mixture is then sifted through a sieve with a mesh size preferably in the range of about 80 mesh to about 100 mesh to ensure a generally uniform composition of particles.

The tablet can be of any desired size, shape, weight, or consistency. The total combined weight of an *Areca* extract composition and a maté extract composition in the form of a dry flowable powder in a single oral dosage is typically in the range of about 80 mg to about 600 mg. An important consideration is that the tablet is intended to dissolve in the mouth and should therefore not be of a shape that encourages the tablet to be swallowed. The larger the tablet, the less it is likely to be accidentally swallowed, but the longer it will take to dissolve or disintegrate. In a preferred form, the tablet is a disk or wafer of about ⅛ inch to about ¾ inch in diameter and about 0.2 inch to 0.08 inch in thickness, and has a weight of between about 160 mg to about 1,200 mg. In addition to disk, wafer or coin shapes, the tablet can be in the form of a cylinder, spher, cube, or other shapes. For example, the tablet can be formed into the general shape of a maté plant leaf. Although the tablet is preferably homogeneous, the tablet may alternatively be comprised of regions of powdered *Areca catechu* extract composition and maté extract composition separated by non-*Areca catechu* and maté extract regions in periodic or non-periodic sequences, which can give the tablet a speckled appearance with different colors or shades of colors associated with the *Areca catechu* and maté extract regions and the non-*Areca catechu* and maté extract regions An exemplary tablet contains about 250.0 mg powdered *Areca* and maté extract, about 12.5 mg extract of Stevia, about 35.5 mg carboxymethylcellulose, and about 77.0 mg lactose. Another exemplary tablet contains about 350.0 mg powdered *Areca* and maté extract, about 15.0 mg extract of Stevia, about 15.0 mg acacia, and about 160.0 mg lactose. Other formulations are also possible. An exemplary tablet contains about 200 mg of *Areca* extract composition, about 100 mg of theobromine, about 12.5 mg extract of Stevia, about 35.5 mg carboxymethylcellulose, and about 77.0 mg lactose. Another exemplary tablet contains about 100 mg of *Areca* extract composition, about 200 mg of theobromine, about 12.5 mg extract of Stevia, about 35.5 mg carboxymethylcellulose, and about 77.0 mg lactose. Other formulations are also possible.

The present invention comprises methods of using compositions comprising combinations of *Areca* extract compositions and maté extract compositions, or *Areca* extract compositions and theobromine compositions, disclosed herein. Methods of providing dietary supplementation are contemplated. Such compositions may further comprise vitamins, minerals and antioxidants. Compositions taught herein can also be used in methods of treatment of conditions wherein a diuretic, relaxant or vasodilator would be effective. For example, the present invention comprises methods of treatment of asthma or obstructive pulmonary disease (COPD), comprising administering an effective amount of a combination composition taught herein Methods of treatment of conditions in which a stimulant to the central nervous system would be effective or treatment of rheumatic conditions are also contemplated by the present invention.

The compositions of the present invention are useful in methods of providing antioxidant activity to cells. It is well recognized that oxygen radicals are involved in various pathologies and that antioxidants protect the cells from oxygen radical-induced damage. Pathologies that are related to oxygen radical damage include, but are not limited to, cancer, cardiovascular disorders, arthritis, inflammation and liver diseases. These and other related pathologies are treated by administering an antioxidant effective amount of a composition of the present invention.

The present invention comprises methods for improving cognition, mental focus, and sense of well being as well as treating mental and physical fatigue and as an adjunct for weight reduction. Methods comprise administering an effective amount of the *Areca* extract compositions and maté extract compositions of the present invention. Methods of the present invention also comprise treatments for obesity and methods for enhancing weight loss comprising, administering an effective amount of a composition, such an amount being effective in reduction of weight of an animal. Formulations comprising oral delivery means can be administered to provide effective amounts of *Areca* extract compounds and the maté extract compounds or theobromine. A wide variety of oral delivery system formulations including, but not limited to, tablets, capsules, lozenges, liquids, and emulsions are contemplated by the present invention. The production of such delivery systems are readily achieved by those having skill in the art and by the methods disclosed herein.

Compositions of the present invention comprise oral delivery formulations wherein the amount of the *Areca* alkaloids combined per dose is between about 0.05 mg and about 300 mg. The amount of the combined *Areca* alkaloids per dose may also be between about 1 mg and about 100 mg. Compositions of the present invention may also comprise alkaloid compounds wherein the percentages of arecoline and guvacoline are reduced with a corresponding elevation of arecaidine and guvacine. In such compositions, the amount of arecaidine per dose is between about 0.01 mg and about 100 mg. The amount of arecaidine per dose may also be between about 0.5 mg and about 10 mg.

One or more of the above compositions of *Areca* can be combined with maté extract compositions, or with theobromine, wherein the amount of the *Areca* alkaloids combined is in an amount per dose between about 0.05 mg and about 300 mg. The amount of the *Areca* alkaloids in such compositions may also be between about 1 mg and about 100 mg. Compositions of *Areca* extract and maté extract compositions can also comprise maté extract compositions in an amount between about 0.1 mg and about 750 mg per dose. Such compositions of *Areca* extract and maté can also be between about 10 mg and about 400 mg per dose. Finally, compositions of the present invention can comprise theobromine in an amount per dose between about 0.1 mg and 500 mg, and can also comprise theobromine in an amount per dose between about 10 mg and about 300 mg.

The combined *Areca* and maté or theobromine compositions may be administered daily, for one or more times, for effective treatment of acute or chronic conditions. Alternatively, separate *Areca* and maté compositions may be administered together for one or more times. Such compositions may be administered as a combined composition, or as separate compositions, daily for an indefinite period. One method of the present invention comprises administering at least one time a day a composition comprising *Areca* compounds and maté compounds. Methods also comprise administering such compositions more than one time per day, more than two times per day, more than three times per day and in a range from 1 to 15 times per day. Such administrations may be continuously, as in every day for a period of days, weeks, months or years, or may occur at specific times to treat or prevent specific conditions. For example, a person may be administered *Areca* and maté compositions at least once a day for years to treat obesity, or to enhance mental focus, cognition, and sense of well being.

All terms used herein are considered to be interpreted in their normally acceptable usage by those skilled in the art. Patents and patent applications or references cited herein are all incorporated by reference in their entireties.

The foregoing description includes the best presently contemplated mode of carrying out the invention. This description is made for the purpose of illustrating the general principles of the inventions and should not be taken in a limiting sense. This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLES

Example 1

The following ingredients were mixed for the following formulation:

| | |
|---|---|
| Extract of *Areca catechu* | 100.0 mg |
| Extract of *I. paraguariensis* (mate) | 150.0 mg |
| Stevioside (Extract of Stevia) | 12.5 mg |
| Carboxymethylcellulose | 35.5 mg |
| Lactose | 77.0 mg |
| Total | 375.0 mg |

The extract of *Areca* composition comprises a ratio of arecadine to arecholine by weight of greater than about 1.0. The extract of *I. paraguariensis* comprises a ratio of theobromine to caffeine by weight of greater than 1.0. The tannin content of *Areca* and *I. paraguariensis* is reduced greater than 80% by weight compared to that found in the respective native plant source. The formulation can be made into any oral dosage form and administered daily or up to 6 times per day as needed for the physiological effect (improved mental focus, cognition and sense of well-being, reduction in mental and physical fatigue, and treatment of obesity).

Example 2

The following were mixed for the following formulation:

| | |
|---|---|
| Extract of *Areca catechu* | 100 mg |
| Arecaidine | 4.2 mg |
| Arecholine | 3.2 mg |
| Guvacine | 3.6 mg |
| Extract of *I. paraguariensis* | 70 mg |
| Theobromine | 3.1 mg |
| Caffeine | 2.8 mg |
| Theophylline | 0.3 mg |
| Vitamin C | 15 mg |
| Sucralose | 35 mg |
| Mung Bean Powder 10:1 | 50 mg |
| Mocha Flavor | 40 mg |
| Chocolate Flavor (RT#NV-24,397) | 20 mg |
| Total | 350 mg |

The extract of *Areca catechu* comprises a ratio of arecaidine to arecholine by weight of greater than about 1.0. The extract of *I. paraguariensis* comprises a ratio of theobromine to caffeine by weight of greater than 1.0. The tannin content of *Areca* and *I. parguariensis* is reduced greater than 80% by weight compared to that found in the respective native plant source. The formulation can be made into any oral dosage form and can be administered daily up to 6 times per day as needed for the physiological effect (weight reduction and appetite suppressant, reduced mental and physical fatigue, and improved mental focus, cognition, and sense of well-being).

Example 3

The following were mixed for the a formulation:

| | |
|---|---|
| Extract of *Areca catechu* | 46.0 mg |
| Extract of *I. paraguariensis* | 90.0 mg |
| Theobromine | 52.0 mg |
| Caffeine | 10.0 mg |
| Theophylline | 1.0 mg |
| Vitamin C | 19.7 mg |
| Sucralose | 40.0 mg |
| Mung Bean Powder 10;1 | 30.0 mg |
| Mocha Flavor | 5.3 mg |
| Total | 294.0 mg |

The extract of *Areca catechu* comprises a ratio of arecaidine to arecholine by weight of greater than about 1.0 and a greater than 80% reduction of tannins by weight compared to the natural seed source. Although this formulation has been made as a freeze dried rapid dissolve tablet, the formulation can be made into any oral dosage for and administer daily up to 6 times per day as needed for the physiological effect (weight reduction and appetite suppression, reduced mental and physical fatigue, and improved mental focus, cognition, and sense of well-being). This formulation has been used successfully to provide the beneficial effects without any deleterious secondary effects having been observed.

What is claimed is:

1. A composition for enhancing memory, cognition, and sense of well being comprising an effective amount of a combination of:
   (a) an *Areca catechu* extract having an altered alkaloid profile comprising arecaidine and arecoline, wherein the concentration of arecaidine is greater than the concentration of arecoline therein, and
   (b) a maté extract comprising theobromine and little or substantially no caffeine, wherein the concentration of caffeine is less that the concentration of theobromine therein.

2. The composition of claim 1, wherein in the *Areca catechu* extract comprises a greater amount of carboxy acid alkaloid compounds than ester alkaloid compounds therein.

3. The composition of claim 1, wherein the *Areca catechu* extract comprises substantially no arecoline.

4. The composition of claim 1, wherein the *Areca catechu* extract comprises substantially no tannin compounds.

5. The composition of claim 1, wherein the maté extract comprises a caffeine concentration that is less than the caffeine concentration of native maté plant material.

6. The composition of claim 1, wherein the maté extract comprises a concentration of tannin compounds that is less that the concentration of tannin compounds found in native maté plant material.

7. A method for enhancing memory, cognition, and sense of well being, comprising,
   administering to a human or animal an effective amount of a composition comprising a combination of:
   (a) an *Areca catechu* extract having an altered alkaloid profile comprising arecaidine and arecoline, wherein the concentration of arecaidine is greater than the concentration of arecoline therein, and (b) a maté extract comprising theobromine and little or substantially no caffeine, wherein the concentration of caffeine is less that the concentration of theobromine therein.

8. The method of claim 7, wherein the *Areca* extract comprises alkaloid compounds in an amount between 0.5 mg and 300 mg.

9. The method of claim 7, wherein the *Areca* extract comprises arecaidine in an amount between 0.01 mg and 100 mg.

10. The method of claim 7, wherein the maté extract comprises an amount between 0.1 mg and 750 mg.

11. The method of claim 7, wherein the is between 0.1 mg and 500 mg, and whereby the maté extract has substantially no caffeine therein.

12. The method of claim 11, wherein the maté extract further comprises substantially no tannin compounds.

13. The method of claim 11, and the amount of theobromine has been omitted and replaced with the phrase
the amount of theobromine within the composition is between 0.1 mg and 500 mg.

14. A method for suppressing appetite and for treating obesity, comprising,
administering to a human or animal an effective amount of a composition comprising a combination of:

(a) an *Areca catechu* extract having an altered alkaloid profile comprising arecaidine and arecoline, wherein the concentration of arecaidine is greater than the concentration of arecoline therein, and (b) a maté extract comprising theobromine and little or substantially no caffeine, wherein the concentration of caffeine is less that the concentration of theobromine therein.

15. The method of claim 14, wherein in the *Areca catechu* extract comprises a greater amount of carboxy acid alkaloid compounds than ester alkaloid compounds therein.

16. The method of claim 14, wherein the *Areca catechu* extract comprises substantially no arecoline.

17. The method of claim 14, wherein the *Areca catechu* extract comprises substantially no tannin compounds.

18. The method of claim 1, wherein the maté extract comprises a caffeine concentration that is less than the caffeine concentration of native maté plant material.

19. The method of claim 14, wherein the maté extract comprises a tannin compounds concentration that is less than the tannin compounds concentration of native maté plant material.

* * * * *